United States Patent
Green et al.

(10) Patent No.: US 8,029,507 B2
(45) Date of Patent: Oct. 4, 2011

(54) ORTHOPEDIC METHOD FOR CORRECTING ANGULAR BONE DEFORMITY

(75) Inventors: Daniel W. Green, Bronx, NY (US); Joseph L. Molino, Valley Cottage, NY (US)

(73) Assignee: Pega Medical, Inc., Laval, Quebec (CA)

( * ) Notice: Subject to any disclaimer, the term of this patent is extended or adjusted under 35 U.S.C. 154(b) by 0 days.

(21) Appl. No.: 12/583,515

(22) Filed: Aug. 21, 2009

(65) Prior Publication Data

US 2010/0004652 A1    Jan. 7, 2010

Related U.S. Application Data

(62) Division of application No. 11/024,208, filed on Dec. 27, 2004, now abandoned.

(51) Int. Cl.
*A61B 17/56* (2006.01)
*A61B 17/58* (2006.01)
*A61B 17/80* (2006.01)
*A61B 17/30* (2006.01)

(52) U.S. Cl. .............. 606/71; 606/280; 606/75

(58) Field of Classification Search .............. 606/280, 606/71, 283, 284, 286
See application file for complete search history.

(56) References Cited

U.S. PATENT DOCUMENTS

| 2,406,832 | A  | * | 9/1946  | Hardinge ................. 606/71 |
| 3,695,259 | A  | * | 10/1972 | Yost ..................... 606/288 |
| 4,686,743 | A  | * | 8/1987  | Suska .................... 16/389 |
| 6,340,362 | B1 | * | 1/2002  | Pierer et al. ............. 606/71 |
| 2003/0139746 | A1 | * | 7/2003 | Groiso ................... 606/75 |
| 2004/0111089 | A1 |   | 6/2004 | Stevens et al. |

OTHER PUBLICATIONS

An Office Action dated Jun. 11, 2008 issued by the PTO for U.S. Appl. No. 11/024,208, filed Dec. 27, 2004.
An Office Action dated Feb. 27, 2009 issued by the PTO for U.S. Appl. No. 11/024,208, filed Dec. 27, 2004.

* cited by examiner

*Primary Examiner* — Thomas C Barrett
*Assistant Examiner* — Christine L Nelson
(74) *Attorney, Agent, or Firm* — Lawrence G. Fridman

(57) ABSTRACT

An orthopedic device and method for correcting angular deformation of a bone structure having a growth plate. The device includes first and second hinge members connected together at a hinge joint. The device is adapted for mounting the orthopedic device to the bone structure with the pivot joint positioned over the growth plate. Alignment of the pivot joint with the growth plate promotes asymmetric growth of the growth plate to thereby correct the angular deformation.

14 Claims, 8 Drawing Sheets

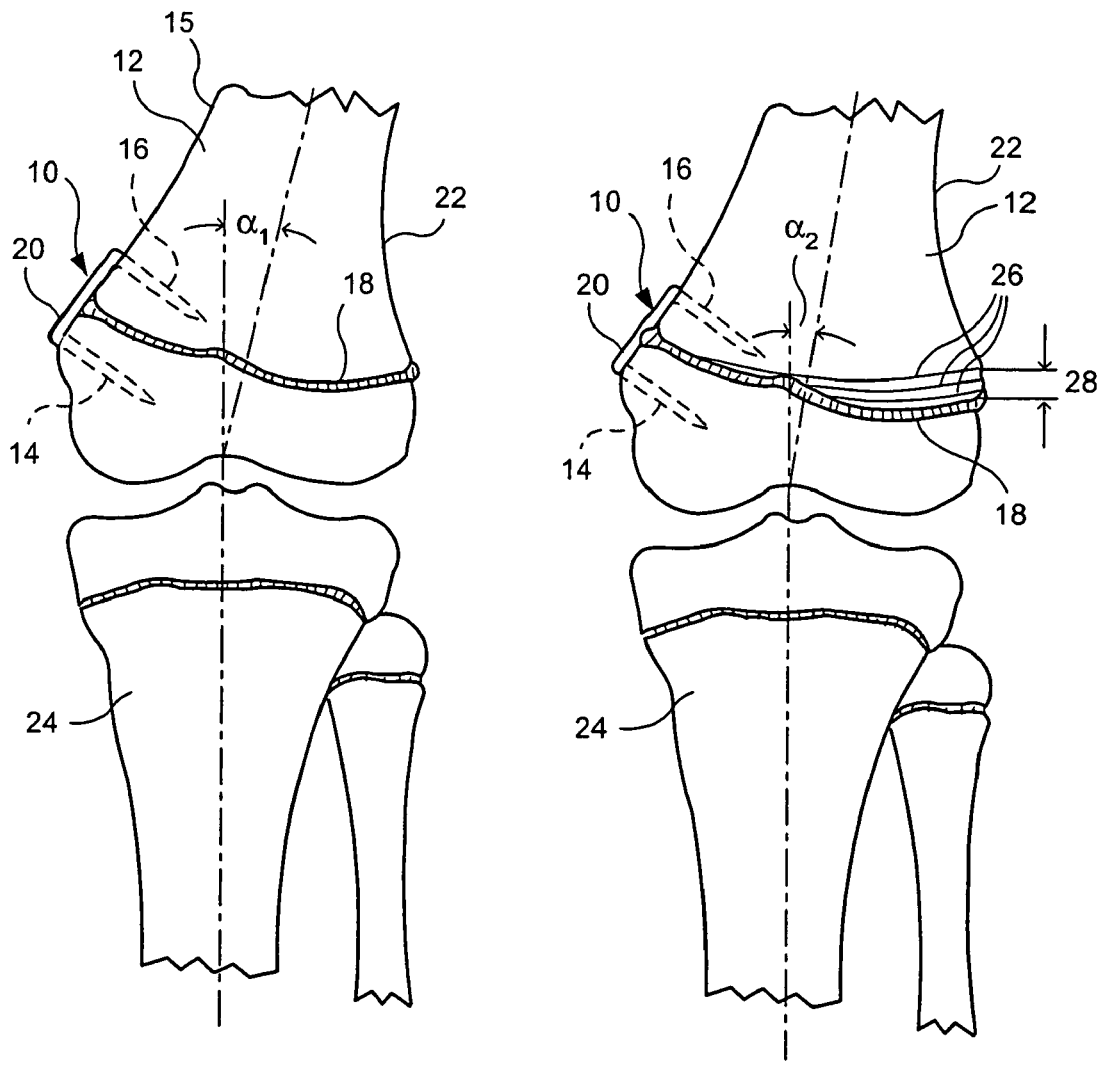
FIG. 1A
PRIOR ART
FIG. 1B
PRIOR ART
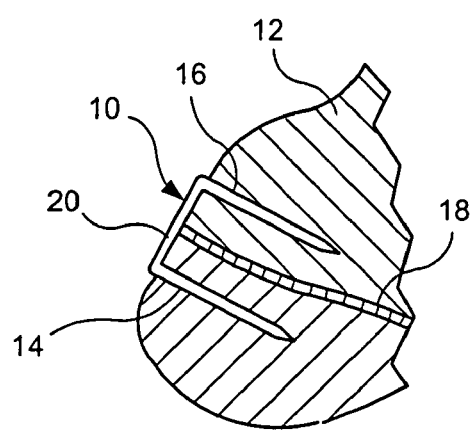
FIG. 1C
PRIOR ART

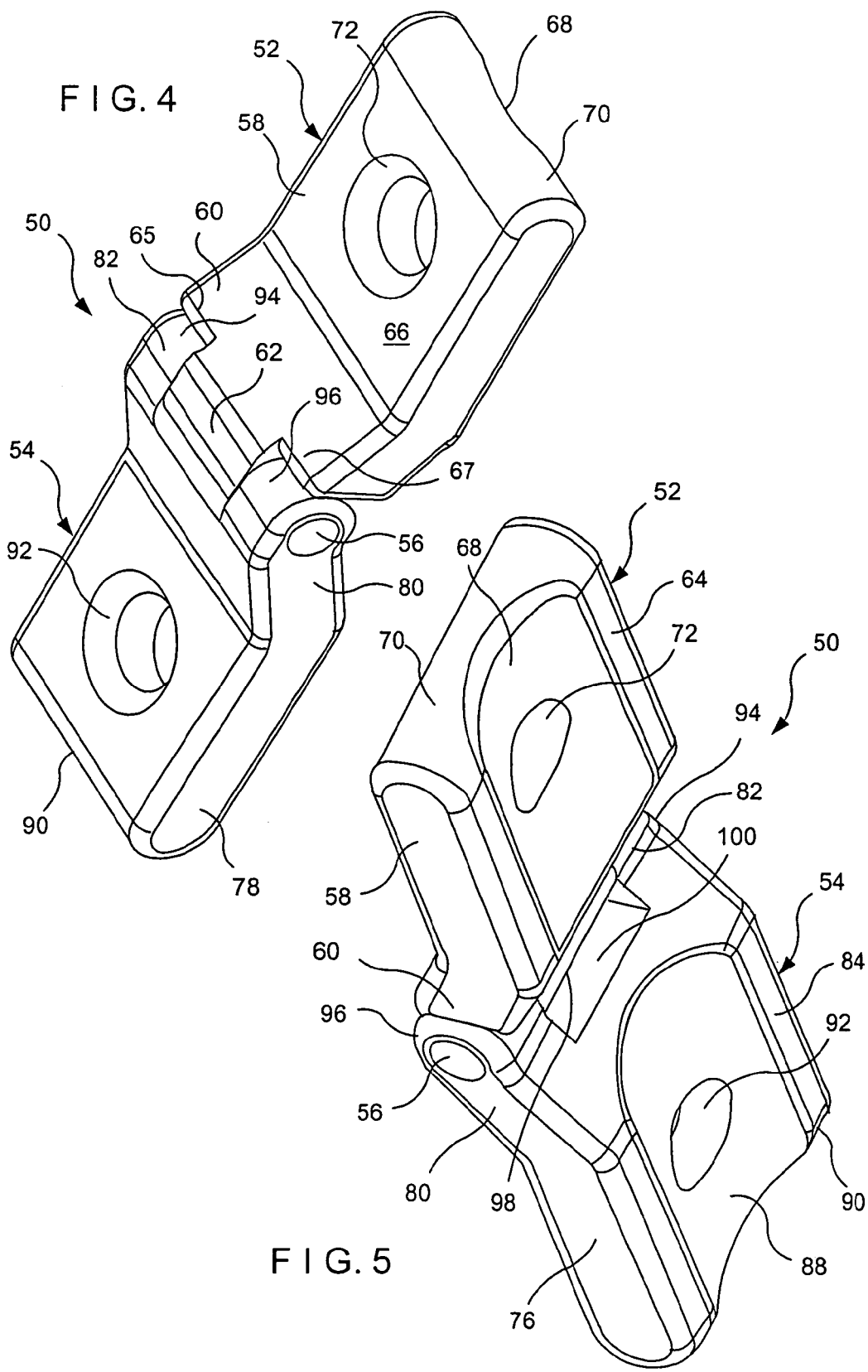

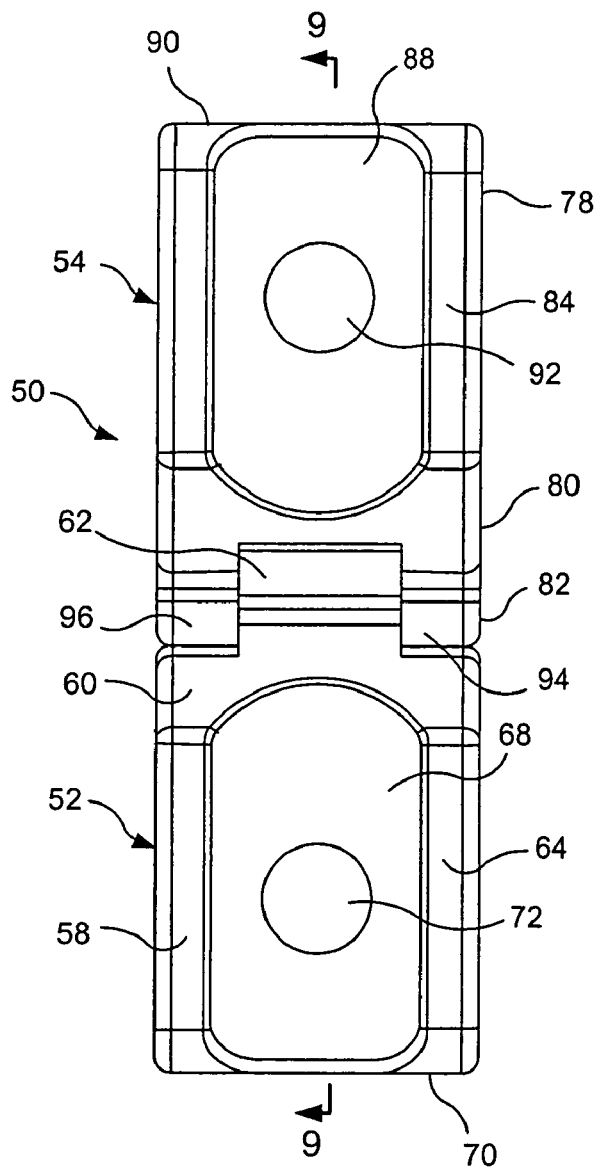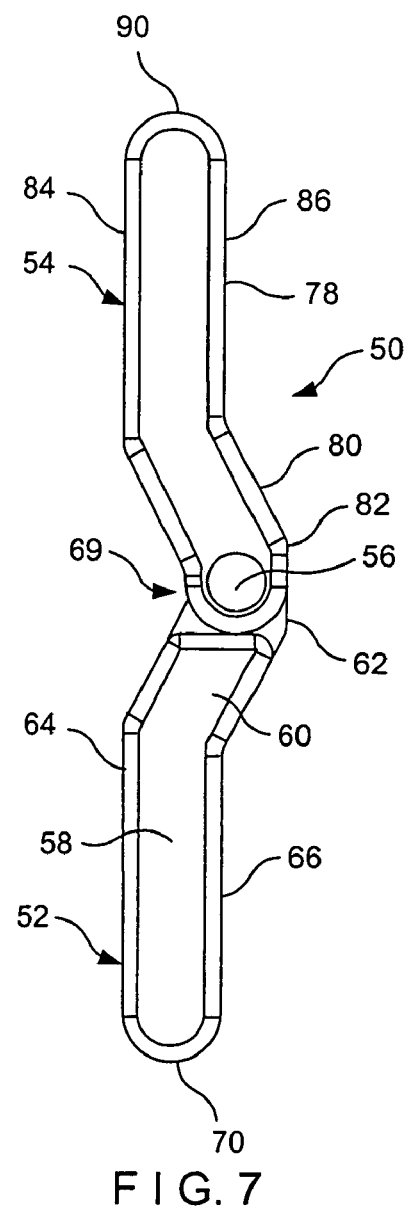
FIG. 6
FIG. 7
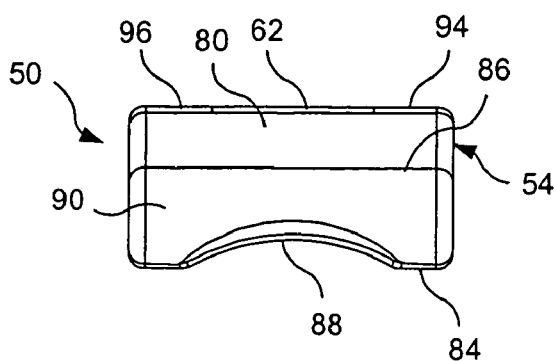
FIG. 8

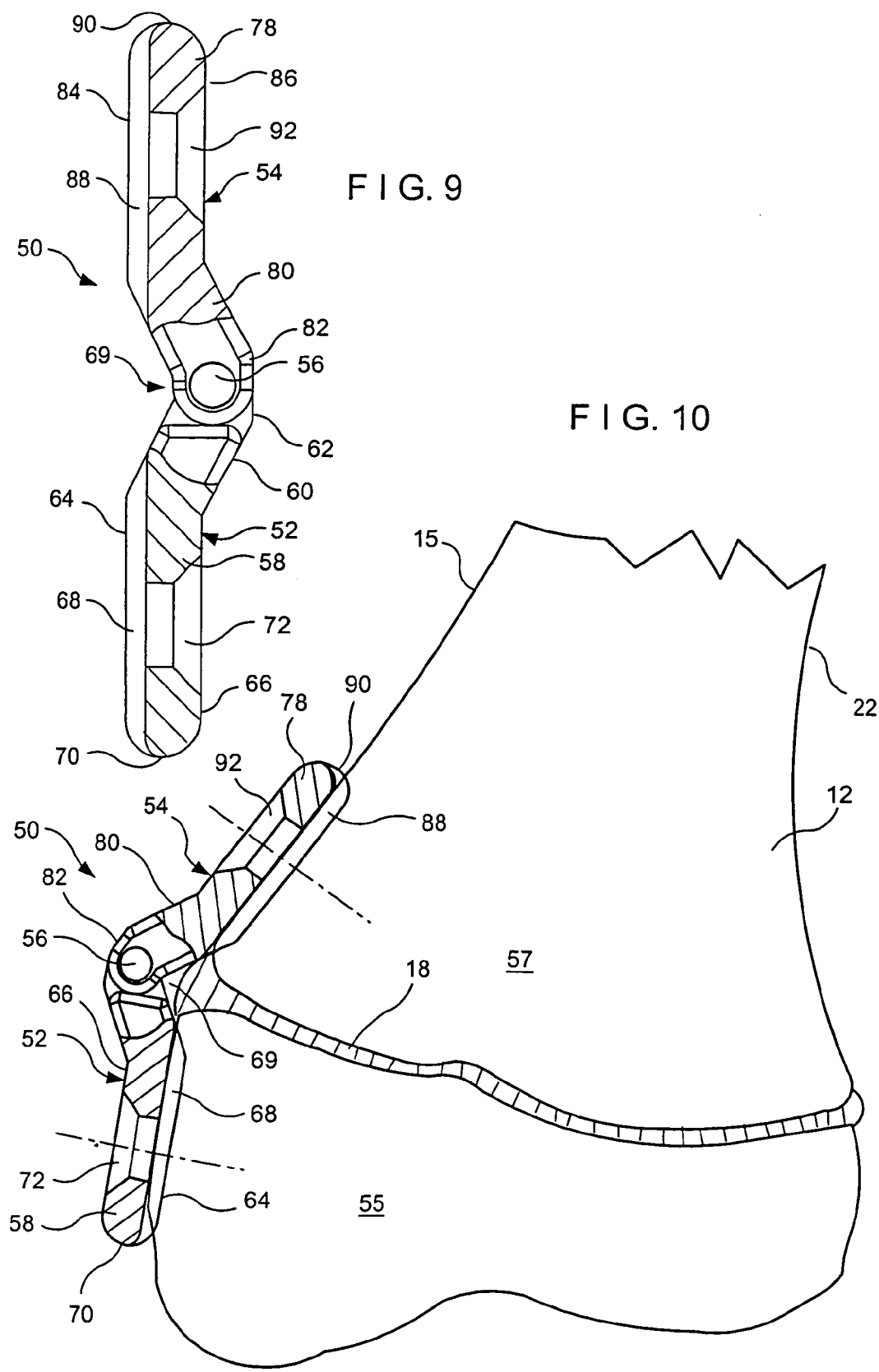

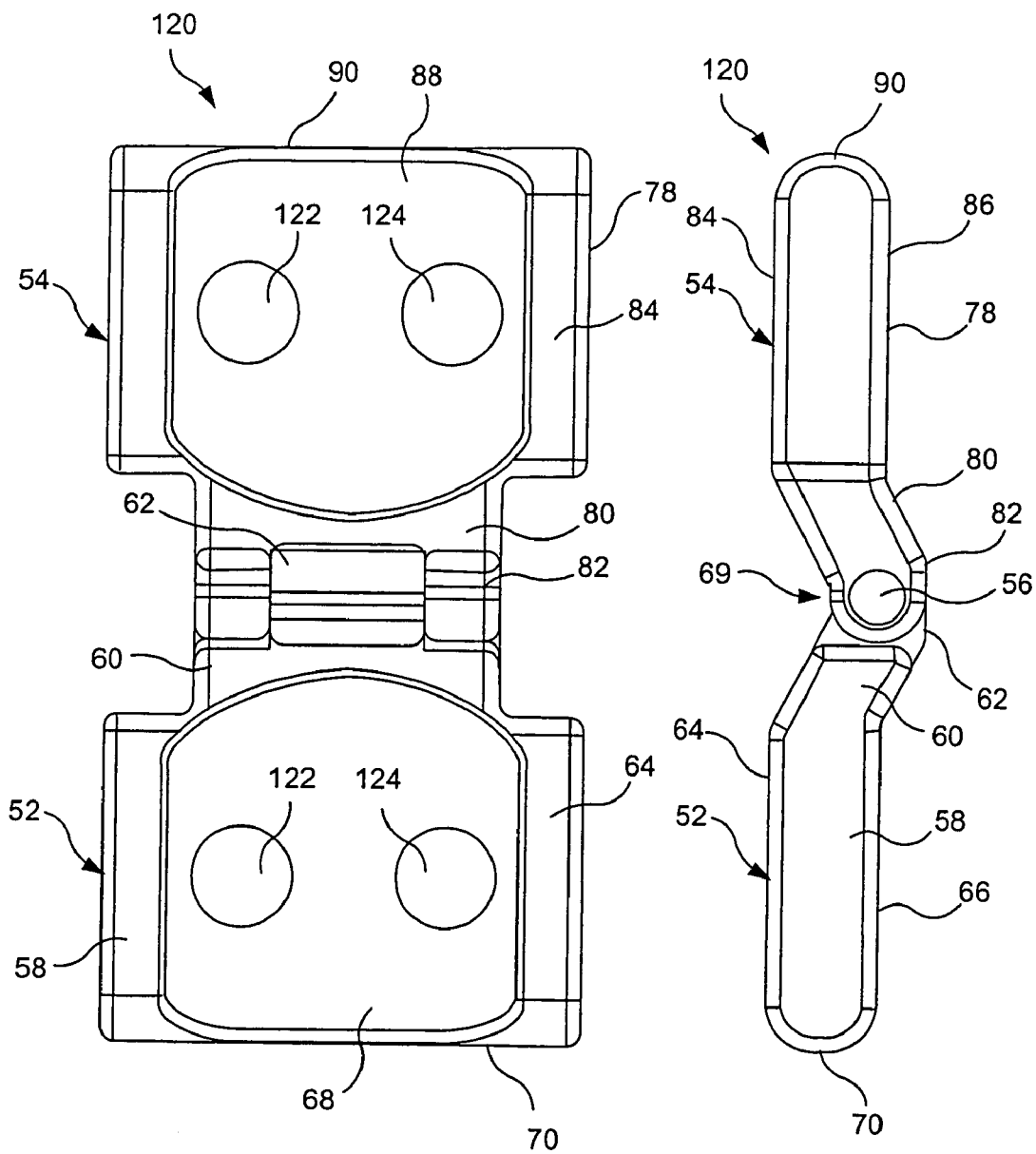
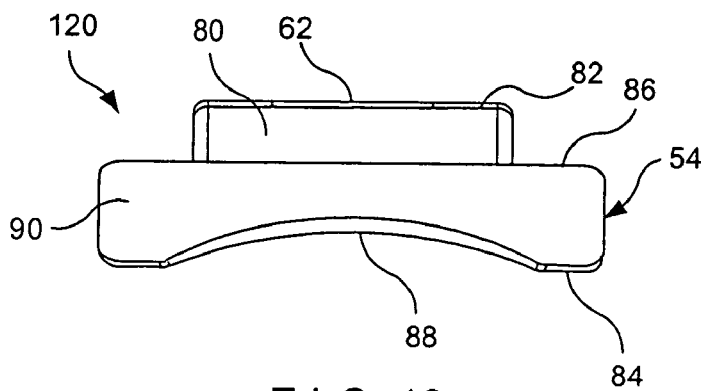
FIG. 11    FIG. 12
FIG. 13

ORTHOPEDIC METHOD FOR CORRECTING ANGULAR BONE DEFORMITY

This Application is a Divisional Application of currently application Ser. No. 11/024,208 filed Dec. 27, 2004 now abandoned

BACKGROUND OF THE INVENTION

This invention relates to correcting angular bone deformities, and more particularly to an orthopedic device and method for correcting angular deformities of the lower extremities, such as genu varus and genu valgus conditions.

Angular bone deformities of the lower extremities are typically characterized by abnormal angulations of the lower leg in relation to the thigh. For example, genu varum is characterized by an abnormal outward bowing of the leg resulting in bowlegs, while genu valgum is characterized by an inward bowing of the leg and is commonly referred to as knock-knees. Under normal conditions, the femur and tibia meet at a tibial-femoral angle of approximately 5-12 degrees of valgus. A greater angle results in a genu valgus condition while a lesser angle results in a genu varum condition. Either of these conditions in one or both legs may result in improper load distribution on the knee joint, causing swelling, knee pain, loss of stability, subluxation, increased joint arthritis, and other conditions that restrict one's lifestyle.

Angular bone deformities in young children can be caused by the following conditions, which are by no means exhaustive: Blount disease, Cerebral Palsy, Larsen's Syndrome, dysplastic disorders, rickets, chronic inflammatory arthritis, neuromuscular causes of hypotonia and fractures.

Various procedures have been developed for treating genu varum and genu valgum in young patients, such as children and adolescents that have not reached full growth. One such procedure is known as cuneiform or wedge osteotomy in which a wedge-shaped section of bone is surgically removed to allow realignment of the bone. The wedge cut made by the surgeon should not completely sever the tibia so that a bridge of residual bone is intact to effectually serve as a hinge for reduction of the wedge-shaped gap that remains following removal of the bone wedge. The depth of the wedge is critical in that if the wedge is too shallow, thus rendering the bridge too wide, the resulting wide fulcrum results in over stressing of the medial cortex during wedge compression, causing fracture of the bone bridge. If the wedge is too deep (the residual bone bridge is too narrow) the residual bone bridge, if not completely severed, may lack sufficient strength to provide medial stability to the reduced osteotomy. Reduction of the wedge-shaped gap allows realignment of the bone, and correction of the loading patterns of the leg. Bone plates are then installed to secure the reshaped bone, at least through the healing process. Although this technique has proven widely successful for adults that have no other recourse or for severe deformities that cannot be corrected by any other means, it is preferable to use less invasive procedures for children and adolescents that have not reached their full stature.

One less invasive procedure for treating the valgus and varus conditions of children or adolescents still in the growth stage includes damaging or destroying one half of the physis or growth plate of the distal femur or proximal tibia by scraping or cutting, with the premise that the undamaged portion will continue to grow in an asymmetric manner to affect the angulation of the lower extremity. However, this technique involves destruction of one half of the growth plate and therefore not a viable option for all patients.

Another less invasive procedure is known as hemiepiphyseal stapling. The principal steps of this procedure are as shown in FIGS. 1A-1C. For a genu valgus condition, a staple 10 is driven into the lateral side 15 of the distal femur 12 about the distal femur physis or growth plate 18. For a genu varus condition, the staple 10 would alternatively be driven into the medial side 22 of the distal femur 12 about the growth plate 18. Other locations for stapling may include the lateral or medial sides of the proximal tibia 24. The staple 10 has two prongs 14, 16 that straddle the distal femur growth plate 18 and a cross member 20 that extends between the prongs 14, 16. Typically, the prongs are oriented perpendicular to the cross member 20. Depending on the age and amount of angular deformity, more than one staple may be used. Ideally, the staple 10 with its prongs 14, 16 promote asymmetric growth on the medial side of the growth plate 18, while inhibiting growth on the lateral side of the growth plate 18 as shown by growth lines 26 and growth distance 28 in FIG. 1B, to thereby reduce the initial tibial-femoral angle $a_1$ (FIG. 1A) to a more acceptable angle $a_2$ (FIG. 1B)

Although hemiepiphyseal stapling is, in some instances, advantageous over other techniques, it suffers from numerous drawbacks. For optimal bone angle correction, growth of the physis should be inhibited on one and unrestricted on the opposite side. However, since the staple 10 must have prongs 14, 16 of sufficient length to ensure firm anchorage into the distal femur, more of the physis may be restricted from growth than desired, leading to less bone angle correction. By way of example, if the prongs extend approximately ⅓ distance into the bone, than approximately ⅓ of the physis will be restricted from growth due to prong resistance. If the stapling procedure is performed toward the end of the growth cycle (13-15 years of age for girls and 16-17 years of age for boys) and does not produce the desired results, then more invasive procedures, such as wedge osteotomy as described above, may have to be performed.

In addition, the staple itself must be inserted with extreme caution, and always in conjunction with radiography to ensure that the ends of the prongs are sufficiently spaced from the growth plate to prevent its damage. Moreover, the dense fibrous tissue (known as the perichrondial ring of LaCroix) that surrounds, anchors and supports the physis during the growth phase may become permanently damaged by the cross member 20 if the staple 10 is inserted too far into the bone.

It would therefore be desirous to provide an orthopedic implant and method for correcting angular bone deformity which minimizes or eliminates the deficiencies of the prior art devices and techniques. It would be further desirous to provide the orthopedic implant and method which promotes asymmetric growth of the growth plate without damaging fibrous tissue by means of a pivotal motion of one part of the device relative to another.

BRIEF SUMMARY OF THE INVENTION

One aspect of the present invention provides an orthopedic device for correcting angular deformation of a bone structure having a first bone portion separated from a second bone portion by a growth plate. The orthopedic device includes first and second hinge members that are pivotally connected together at a pivot joint. The first hinge member is adapted for connection to the first bone portion and the second hinge member is adapted for connection to the second bone portion. Alignment of the pivot joint with the growth plate promotes asymmetric growth of the growth plate to thereby correct the angular deformation.

Another aspect of the present invention provides a method of correcting angular deformation of a bone structure having a first bone portion separated from a second bone portion by a growth plate. The method comprises providing an orthopedic device having a first hinge member pivotally connected to a second hinge member at a pivot joint, aligning the pivot joint with the growth plate, and mounting the first and second hinge members to the first and second bone portions, respectively. In this manner, alignment of the pivot joint with the growth plate promotes asymmetric growth of the growth plate to thereby correct the angular deformation.

BRIEF DESCRIPTION OF THE DRAWINGS

The foregoing summary as well as the following detailed description of the preferred embodiments of the present invention will be best understood when considered in conjunction with the accompanying drawings, wherein like designations denote like elements throughout the drawings, and wherein:

FIG. 1A is a front elevational view of a distal femur and proximal tibia and fibula with their respective growth plates and a prior art hemiepiphyseal stapling technique for encouraging asymmetric growth of the distal femoral growth plate;

FIG. 1B is a view similar to FIG. 1A showing limited asymmetric growth of the distal femoral growth plate resulted from use of a staple;

FIG. 1C is a sectional view of the prior art hemiepiphyseal stapling technique;

FIG. 4 is a front perspective view of the orthopedic device in accordance with the present invention;

FIG. 5 is a rear perspective view of the orthopedic device;

FIG. 6 is a rear elevational view of the orthopedic device;

FIG. 7 is a side elevational view of the orthopedic device;

FIG. 8 is a top plan view of the orthopedic device;

FIG. 9 is a sectional view of the orthopedic device taken along section line 9-9 of FIG. 6;

FIG. 10 is a sectional view of the orthopedic device positioned on the distal femur and aligned with the distal femoral growth plate;

FIG. 11 is a is a rear elevational view of an orthopedic device in accordance with a further embodiment of the invention;

FIG. 12 is a side elevational view of the orthopedic device of FIG. 11;

FIG. 13 is a top plan view of the orthopedic device of FIG. 11; and

It is noted that the drawings are intended to depict only typical embodiments of the invention and therefore should not be considered as limiting the scope thereof. It is further noted that the drawings are not necessarily to scale. The invention will now be described in greater detail with reference to the accompanying drawings.

DETAILED DESCRIPTION OF THE INVENTION

Figure 2A:
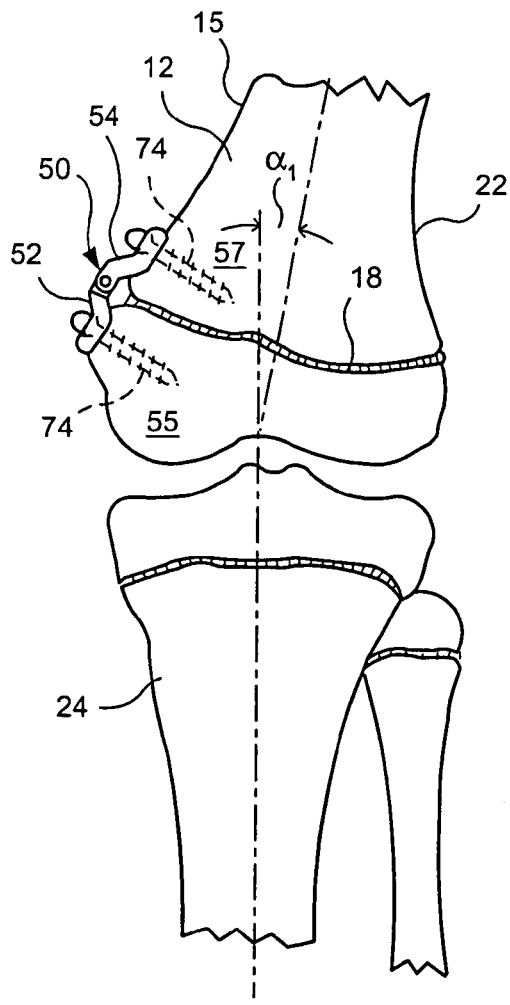
FIG. 2A is an anterior front elevational view of a distal femur and proximal tibia and fibula with their respective growth plates and an implanted orthopedic device in accordance with the present invention for encouraging asymmetric growth of the distal femoral growth plate.
Figure 2B:
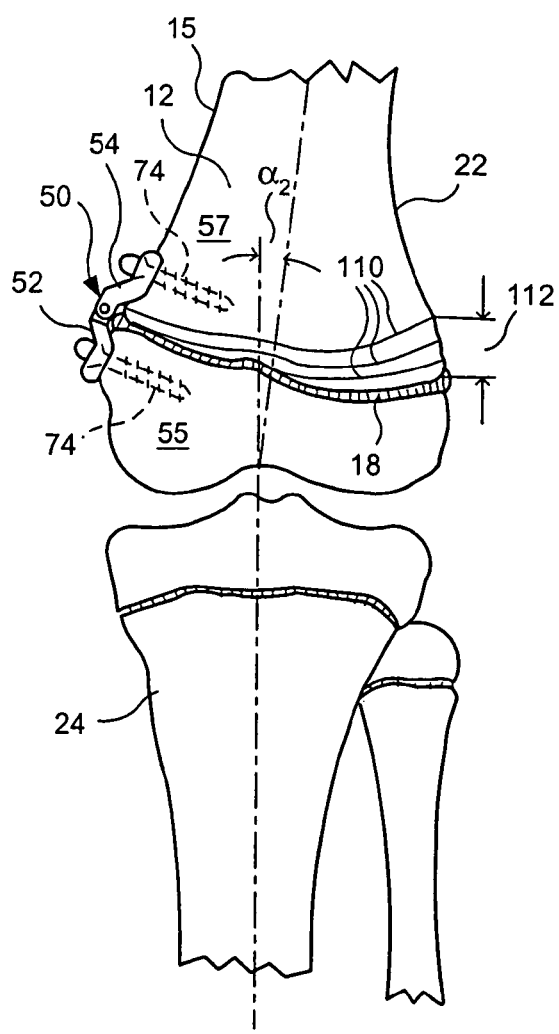
FIG. 2B is a is a view similar to FIG. 2A showing asymmetric growth of the distal femoral growth plate.
Figure 2C:
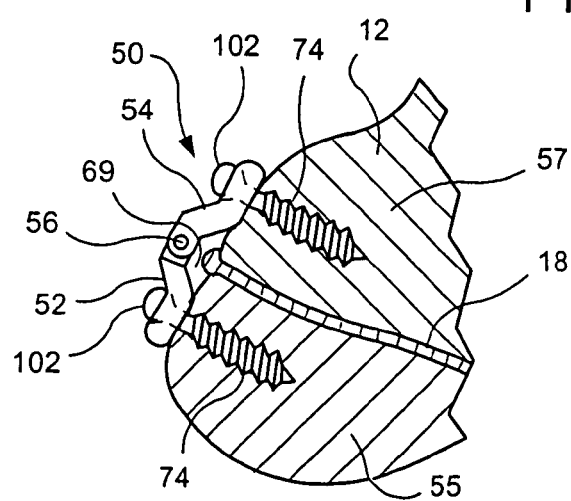
FIG. 2C is a is a sectional view of the distal femoral growth plate and surrounding bone with the implanted orthopedic device in accordance with the present invention.

Referring to the drawings and to FIGS. 2A-2C in particular, wherein a procedure for correcting a genu valgus condition in accordance with an exemplary embodiment of the present invention is illustrated. The procedure includes installing a unique orthopedic device 50 onto the lateral side 15 of the distal femur 12 about the distal femur physis or growth plate 18. For a genu varus condition, the orthopedic device 50 would alternatively be mounted onto the medial side 22 of the distal femur 12 about the growth plate 18. Other locations that may be suitable for installing the orthopedic device 50 may include, without limitation, the growth plate region of proximal tibia, distal tibia, proximal femur, as well as locations on the humerous, ulna and/or radius and spinal formation.

With further reference to FIGS. 4-10, the orthopedic device 50 includes a first substantially rigid hinge plate 52 pivotally connected to a second substantially rigid hinge plate 54 by means of a hinge pin 56. The plates 52, 54 are preferably generally rectangular in shape, although other shapes, such as triangular, circular, and so on are also contemplated.

The first hinge plate 52 is formed with a bone mounting portion 58, a ramped portion 60 extending at an angle from the bone mounting portion, and a hinge portion 62 extending from the ramped portion. The bone mounting portion 58 includes an inner surface 64 that faces the bone when mounted to a patient and an outer surface 66 that faces away from the bone. A channel 68 is formed in the inner surface 64 and extends substantially from a distal end 70 of the first hinge plate 52 to the ramped portion 60. As best shown in FIG. 10, to facilitate positioning and alignment of the first hinge plate 52, the shape of the channel 68 is preferably at least partially complementary to the shape of the bone portion to which the hinge plate 52 will be mounted. Accordingly, it will be understood that the channel 68 can take on a variety of different shapes. It will be further understood that, if necessary, the channel 68 may be eliminated. A chamfered opening 72 extends through the first hinge plate 52 from the outer surface 66 to the channel 68. The opening 72 is preferably centrally located in the bone mounting portion 58 and is adapted to receive a fastener 74 (see for example FIG. 2A-2C) for securing the first hinge plate 52 to the respective bone structure.

The hinge portion 62 includes a bore (not shown) that extends therethrough for accommodating the hinge pin 56. Preferably, the inner diameter of the bore is greater than an outer diameter of the hinge pin 56, so that the first hinge plate 52 can rotate freely about the hinge pin. The ramped portion 60—hinge portion 62 interface is in the form of a single energizing element extending outwardly from the plate 52, so that two shoulders 65, 67 are formed on both sides thereof.

The second hinge plate 54 has a bone mounting portion 78, a ramped portion 80 extending at an angle from the bone mounting portion 78, and a bifurcated hinge portion 82 extending from the ramped portion. The bone mounting portion 78 includes an inner surface 84 that faces the respective bone structure, when mounted to a patient, and an outer surface 86 that faces away from the bone. A channel 88 is formed in the inner surface 84 and extends substantially from a distal end 90 of the second hinge plate 54 to the ramped portion 80. As best illustrated in FIG. 10, to facilitate positioning and alignment of the second hinge plate 54, the shape of the channel 88 is preferably at least partially complementary to the shape of the respective bone portion. Accordingly, it will be understood that the channel 88 can take on a variety of different shapes, and may be different in configuration from the shape of the channel 68 of the first hinge plate 52. It will be further understood that, if it is necessary, the channel 88 may be eliminated. A chamfered opening 92 extends through the second hinge plate 82 from the outer surface 86 to the channel 88. The opening 92 is preferably centrally located in the bone mounting portion 78 and is adapted to receive a fastener 74 (see for example FIGS. 2A-2C) for securing the second hinge plate 54 to the bone.

The bifurcated hinge portion 82 includes spaced arms 94, 96 and a bore (not shown) extending through each arm for accommodating the hinge pin 56. Preferably, the inner diameter of the bore is less than or equal to an outer diameter of the hinge pin 56. In this manner the hinge pin 56 can be press-fit into the spaced arms 94, 96 and held against rotation with respect to the second hinge plate 54. The arms 94, 96 are sufficiently spaced to movably receive the single element hinge portion 62 of the first hinge plate 52 therebetween. In the assembled condition, the ramped portions 60, 80 and hinge portions 62, 82 of the first and second hinge plates form an operational recess 69 extending inwardly from the planes of the inner surfaces 64, 84.

As shown in FIG. 5, a first stop surface 98 is formed on the hinge portion 62 of the first hinge plate 52 and a corresponding second stop surface 100 is formed on the hinge portion 62 between the arms 94, 96 of the second hinge plate 54. The first and second stop surfaces 98, 100 are arranged to engage and stop relative rotating movement between the hinge plates when a particular rotation angle has been reached. By way of example, it may be desirous to limit the angular correction of the bone deformity to five degrees for one patient, 20 degrees for another patient, 30 degrees for yet another and 45 degrees for still another patient. Thus, the stop surfaces may be dimensioned or otherwise formed as needed to accommodate a particular desired rotational limit. This feature is especially advantageous since overcorrection of the bone deformity is discouraged. Once the required angular bone deformity correction has been achieved and the desired bone angle has been reached, the hinge plates 52, 54 of the orthopedic device 50 will no longer pivot and therefore can be removed from the patient.

As shown in FIGS. 4-10, all corners and ends of the first and second hinge plates are rounded to eliminate sharp edges or protrusions that may otherwise damage surrounding tissue when the orthopedic device 50 is installed in a patient. Preferably, the first and second hinge plates, as well as the hinge pin, are constructed of biocompatible materials, such as surgical stainless steel, titanium or combinations thereof, as well as other materials including metal, ceramic, and/or plastic.

In accordance with an exemplary embodiment of the invention, the orthopedic device 50 can be constructed with a very low profile with a plate thickness of about 2-3 mm and an overall length of about 1.8 cm from the distal end 70 to the distal end 90. However, it will be understood that these dimensions are given by way of example only and that the orthopedic device 50 can greatly vary in size and shape.

With particular reference to FIGS. 2A-2C, 3 and 10, a method of correcting the angular bone deformity, such as the genu varus condition, includes exposing the growth plate 18 and a portion of the distal femur surrounding the growth plate by gaining access to and retracting the overlying soft tissues and muscles. These areas do not have any significant impediments to placement of the orthopedic device 50. Once the soft tissues and muscles have been retracted, the underlying periosteum (dense fibrous membrane covering the surface of bones) is opened. The orthopedic device 50 is then placed on the lateral side 15 of the distal femur 12 such that the first hinge plate 52 abuts a first condyle bone portion 55, the second hinge plate 54 abuts a second condyle bone portion 57, so that the operational recess 69 and the hinge pin 56 or pivot joint are in alignment with the growth plate 18 which is now positioned between the first and second bone portions. Optimum alignment of the pivot joint and the operational recess 69 with the respective portions of the bone structure can be confirmed by direct vision as well as inter-operative radiographs. The rigidity of the hinge plates ensures that the orthopedic device 50 can be mounted with greater control and precision. The precise positioning of the operational recess 69 including the pivot joint at the growth plate 18 is one of the major advantages of the device of the invention over the prior art. Depending on the type of angular deformity to be corrected, it will be understood that the orthopedic device 50 can be positioned on either the lateral or medial side of the bone structure and/or at other locations as previously mentioned, such as the proximal tibia, distal tibia, proximal femur, as well as locations on the humerous, ulna and/or radius Once the orthopedic device 50 is correctly placed over the growth plate with the channel 68, 88 of each hinge plate properly seated on the condyle bone portions of the distal femur, fasteners 70, preferably in the form of bone screws with ball-shaped heads 102, are inserted through the chamfered openings 72, 92 of the hinge plates 52, 54 and screwed into the bone. The provision of screws with ball-shaped heads permits the surgeon to individually and independently orient the screws away from the growth plate and toward the most solid portion of the bone. This feature is a great advantage over prior art stapling since placement of the prongs cannot be individually and independently controlled, and further since the screws lend to a more secure mounting of the orthopedic device 50.

Once the orthopedic device 50 is properly placed and securely mounted to the bone, it can be seen that the operational recess 69 including the ramped portions 60, 80 of the hinge plates 50, 52 ensure that no part of the orthopedic device will come in a substantial contact with the growth plate 18 or the perichrondial ring of LaCroix that surrounds the growth plate to thereby prevent growth plate damage. In addition, the channels 68, 88 of the hinge plates 50, 52 directly engage the bone structure so that very little gap remains between the orthopedic device 50 and the bone. These features are advantageous over prior art stapling since in some instances there tends to be an undesirable substantial gap between the cross member of staple and the bone. In the hemiepiphyseal stapling procedure, when surgeons try to reduce the gap by placing or pushing or hammering the staple deeper into the bone, the cross member 20 that connects the prongs 14, 16 of the prior art staple has a tendency to contact and damage the growth plate (see FIGS. 1A-1C).

Figure 3:
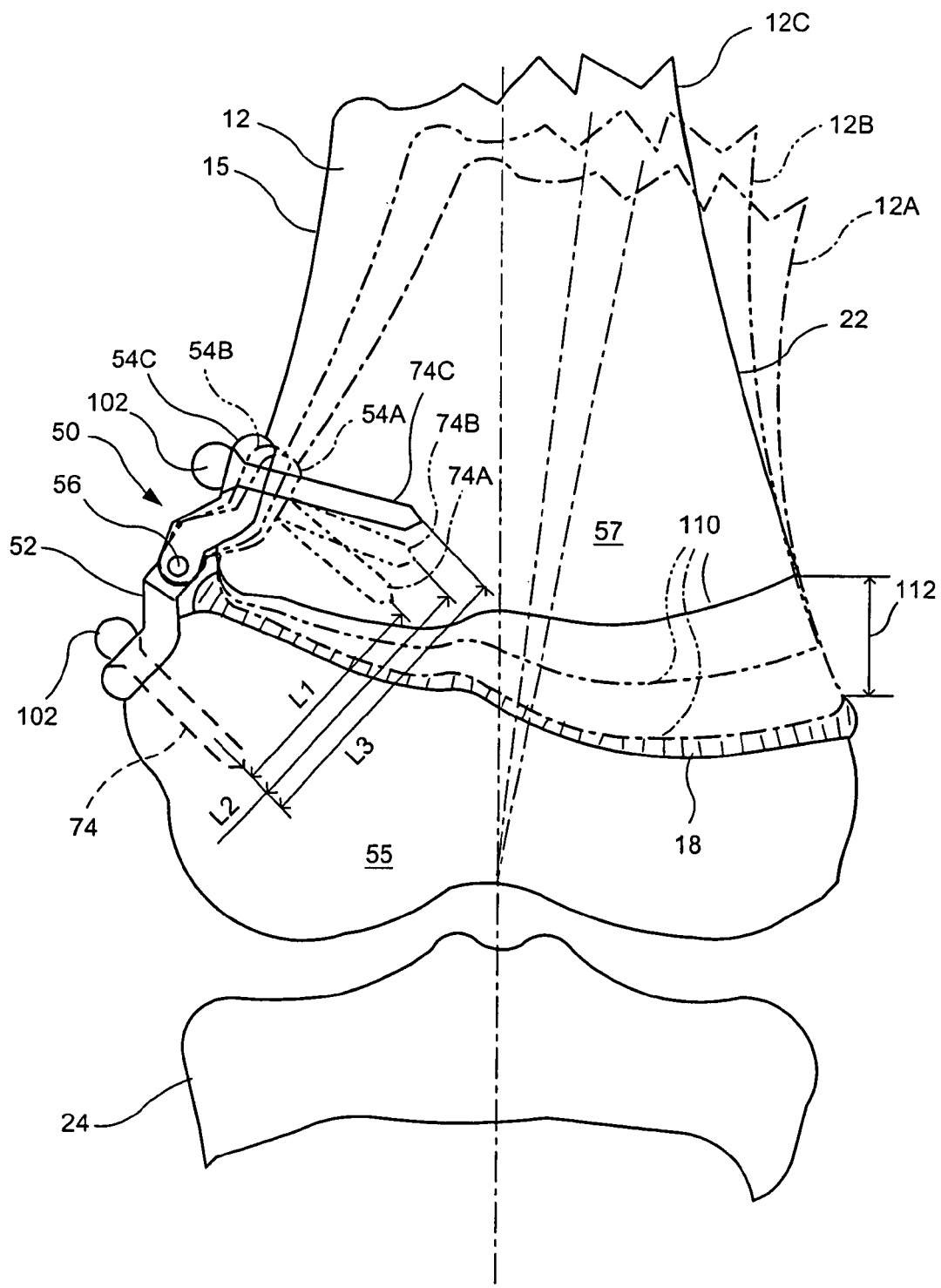
FIG. 3 is an enlarged anterior elevational view similar to FIG. 2A showing various phases of the asymmetric growth and positions of the orthopedic device corresponding to such.

In use, as shown in FIGS. 2A, 2B and 3, the installed orthopedic device 50 promotes asymmetric growth on the medial side of the growth plate 18 while inhibiting growth on the lateral side thereof as shown by growth lines 110 and growth distance 112 to thereby reduce the initial tibial-femoral angle $a_1$ (FIG. 2A) to a more acceptable angle $a_2$ (FIG. 2B). Since the orthopedic device 50 pivots at the lateral side of the growth plate 18, one or both of the fasteners 74 will also rotate with the new asymmetric bone growth as the angular deformity reduces. The second hinge plate movement is illustrated by lines 54A, 54B and 54C, the fastener 74 movement is illustrated by lines 74A, 74B and 74C and the increasing distance between the distal ends of the fasteners is represented by lengths L1, L2 and L3. Movement of the second hinge plate 54 and the fastener 102 associated therewith corresponds to bone growth or movement lines 12A, 12B and 12C in FIG. 3. In view of the ramped portions 60, 80 and operational recess 69 formed there between, the pivotal joint is spaced from but positioned precisely at the growth plate 18. In this manner, the growth of the bone structure at the lateral side of the growth plate 18 is inhibited in the linear or longitudinal direction. However, in view of the pivotal arrangement, the growth and development of the growth plate at the same lateral side in the radial direction is encouraged. Furthermore, since the pivotal joint is spaced from the bone structure the entire area of the growth plate (to a smaller degree at the lateral side and to a greater degree at the medial side) is able to undergo asymmetric or radial growth. This enables the orthotic device of the invention to provide a greater degree of angular correction in an easier, quicker and more controlled manner than in the prior art. In addition, the use of long screws as the fasteners permits the surgeon to precisely place the orthopedic device 50 at the desired location, thus minimizing potential damage to the growth plate while maximizing the mounting strength of the orthopedic device 50 to the bone structure.

Referring now to FIGS. 11-13, an orthopedic device 120 in accordance with a further embodiment of the invention is illustrated. The orthopedic device 120 is similar to the orthopedic device 50 previously described, with the exception that each hinge plate 52, 54 is wider and includes a pair of spaced chamfered openings 122, 124 for receiving fasteners, such as the bone screws previously described. In this manner, the orthopedic device 120 may be more securely mounted to the bone structure. It will be understood that other shapes as well as more or less openings may be provided for each hinge plate.

Figure 14:
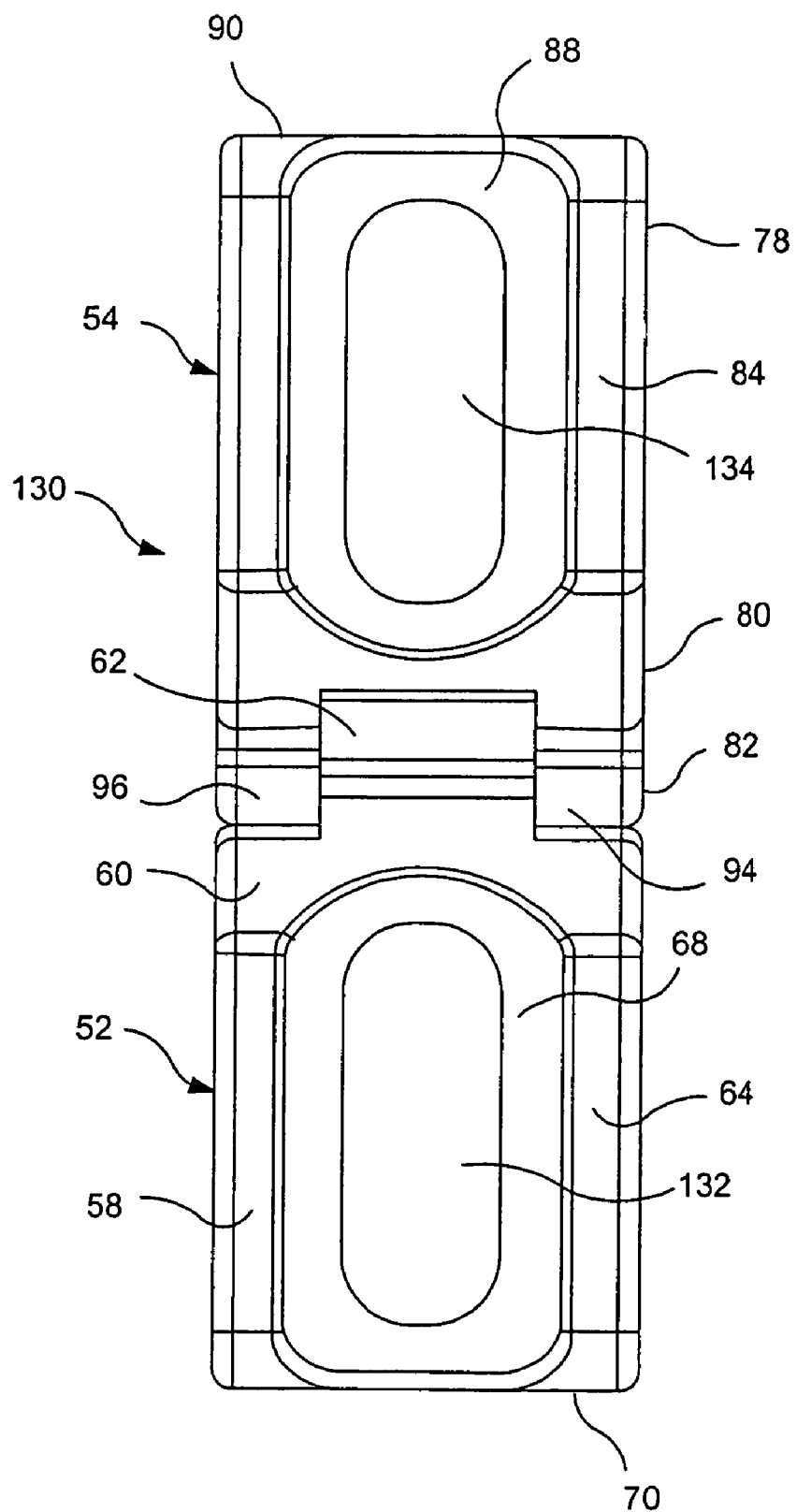
FIG. 14 is a rear elevational view of an orthopedic device in accordance with yet a further embodiment of the invention.

Referring now to FIG. 14 wherein an orthopedic device 130 in accordance with yet a further embodiment of the invention is illustrated. The orthopedic device 130 is similar to the orthopedic device 50 previously described, with the exception that the chamfered opening in each hinge plate 52 and 54 is replaced with an elongate slot 132 and 134, respectively. The elongate slots 132 and 134 preferably extend in the direction of their associated channels 68 and 88, respectively. It should be noted that the slots 132, 134 may be oriented in a direction transverse or perpendicular to the direction of the channels. The elongate slots 132, 134 are especially advantageous during positioning of the orthopedic device 130 on the bone structure. When it has been found by direct vision and/or inter-operative radiograph that the pivot joint is not properly aligned with the growth plate 18, one or more of the fasteners 74 need simply be loosened and the orthopedic device 130 repositioned until the pivot joint is properly aligned over the growth plate. In this manner, very precise alignment can occur without additional stress or injury to the bone structure.

It will be appreciated by those skilled in the art that changes could be made to the embodiments described above without departing from the broad inventive concept thereof. It will be understood, therefore, that this invention is not limited to the particular embodiments disclosed, but is intended to cover modifications within the spirit and scope of the present invention as defined by the appended claims.

What is claimed is:

1. A method of for correcting angular deformities of lower extremities bone structure of children and adolescents having a first bone portion separated from a second bone portion by a growth plate by promoting asymmetric growth by means of an orthopedic device comprising:

a first hinge plate and a second hinge plate connected to each other at a pivot joint for pivotal motion therebetween, each hinge plate further comprising a hinge portion forming a part of the pivot joint, a mounting portion extending in a plane adapted for engagement with the bone structure, and a ramp portion extending within a plane disposed at an angle to the plane of the mounting portion, the pivot portion extending transversely to the planes of the mounting and ramp portions, the ramp and the hinge portions of the first and second hinge plates forming an operational recess therebetween; the method comprising the steps of:

positioning the first and second hinge plates on the first and second bone portions in such a manner that the mounting portions extend substantially along a longitudinal axis of the bone structure to be corrected, and the hinge portions and the pivot joint are positioned transversely to the longitudinal axis;

aligning the pivot joint and the operational recess with the growth plate so that the operational recess extend away from the growth plate, and the pivot joint is separated from the growth plate by a space to facilitate movement of the first and second hinge plates about the pivot joint;

mounting the mounting portions of the first and second hinge plates at the first and second bone portions respectively;

whereby an asymmetric growth on one side of the growth plate is promoted and the growth on an opposite side thereof is inhibited.

2. A method according to claim 1 wherein the mounting step comprises driving at least one fastening member through at least one of the hinge plates and into one of the bone portions.

3. A method according to claim 2, wherein the at least one fastening member is a bone screw and wherein the mounting step further comprises orienting the bone screw in a direction substantially parallel to or away from the growth plate.

4. A method according to claim 1, further comprising providing at least one slot in each of the hinge plates and further wherein the mounting step comprises driving at least one bone screw through at least one of the slots and into one of the bone portions.

5. A method according to claim 4, wherein the aligning step comprises sliding the orthopedic device with respect to the at least one bone screw until the pivot joint is aligned with the growth plate.

6. A method according to claim 5, wherein the at least one bone screw comprises a rounded head and wherein the mounting step comprises orienting the bone screw in a direction substantially parallel to or away from the growth plate to thereby secure the orthopedic device to the bone structure.

7. A method according to claim 1, wherein an inner surface of each said hinge plate is formed with an inwardly extending channel; each said channel is configured to have a shape complimentary to a shape of the respective bone portion, so that in said step of mounting engagement of the channel and the respective bone portion minimizes a gap formed therebetween.

8. A method according to claim 1, wherein the orthopedic device is placed on the lateral side of the distal femur such that the first hinge plate abuts a first condyle bone portion, the second hinge plate abuts a second condyle bone portion, so that the operational recess and the pivot joint are in alignment with and spaced from the growth plate positioned between the first and second condyle portions, so that growth of the bone structure at the lateral side of the growth plate is inhibited in the linear or longitudinal direction, and the growth and development of the growth plate at the same lateral side in the radial or rotational direction is enhanced.

9. A method according to claim 8, wherein the growth plate at the medial side undergoes asymmetric or radial growth, so as to provide a greater degree of angular correction in a controlled manner.

10. A method according to claim 1, wherein the orthopedic device further comprises the first hinge plate being formed with a first stop portion and the second hinge plate formed with a second stop portion, upon being engaged the first and second stop potions are arranged to prevent further relative rotational movement between the hinge plates, said method further comprises the steps of setting a predetermined degree of angular correction of bone deformity and preventing further rotational movement between hinge plates when said predetermine degree of angular correction is reached.

11. A method according to claim 1, wherein the first and second stop portions are formed to accommodate a predetermined rotational limit, so that upon reaching the predetermined degree of angular bone deformity, the first and second stop portions are engaged preventing the respective hinge plates from further rotational movement.

12. The method according to claim 1, wherein there are no substantial contacts between the orthopedic device and the perichrondial ring of LaCroix surrounding the growth plate of the bone structure to be corrected.

13. The method according to claim 1, wherein in the step of mounting inner surfaces of the first and second mounting portions engage the respective bone structure.

14. A method of correcting angular deformities of lower extremities bone structure of children and adolescents having a first bone portion separated from a second bone portion by a growth plate by promoting asymmetric growth by means of an orthopedic device comprising:

a first hinge plate and a second hinge plate connected to each other at a pivot joint for pivotal motion therebetween, each hinge plate further comprising a hinge portion forming a part of the pivot joint, a mounting portion extending in a plane adapted for engagement with the bone structure, and a ramp portion extending within a plane disposed at an angle to the plane of the mounting portion, the pivot portion extending transversely to the planes of the mounting and ramp portions, the ramp and the hinge portions of the first and second hinge plates forming an operational recess therebetween; the method comprising the steps of:

positioning the first and second hinge plates on the first and second bone portions so that the first and second ramp portions extend outwardly in an anterior direction from the growth plate;

aligning the pivot joint with the growth plate, so that the operational recess extends outwardly in the anterior direction from the growth plate and the growth plate is separated from the pivot joint by a space to facilitate movement of the first and second hinge plates about the pivot joint; and mounting the first and second hinge plates at the first and second bone portions respectively, so that the space between the pivot joint and growth plate is maintained to prevent contact between the orthopedic device and at least the growth plate during the correction of angular deformities to thereby minimize the growth plate damage;

whereby asymmetric growth on one side of the growth plate is promoted and growth on an opposite side thereof is inhibited.

* * * * *